(12) United States Patent
Tronnes et al.

(10) Patent No.: US 7,463,934 B2
(45) Date of Patent: Dec. 9, 2008

(54) IMPLANTABLE MEDICAL DEVICE WITH CAPTIVATION FIXATION

(75) Inventors: Carole Tronnes, St. Paul, MN (US); John M. Swoyer, Andover, MN (US); Martin T. Gerber, Maple Grove, MN (US)

(73) Assignee: Medtronic, Inc., Minneapolis ( * ) Notice: Subject to any disclaimer, the term of this patent is extended or adjusted under 35 U.S.C. 154(b) by 577 days.

(21) Appl. No.: 10/121,484

(22) Filed: Apr. 12, 2002

(65) Prior Publication Data

US 2003/0195600 A1 Oct. 16, 2003

(51) Int. Cl.
*A61N 1/36* (2006.01)

(52) U.S. Cl. ...................................... 607/133

(58) Field of Classification Search ................. 600/373, 600/377, 393; 607/2, 40, 116, 133
See application file for complete search history.

(56) References Cited

U.S. PATENT DOCUMENTS

| | | | |
|---|---|---|---|
| 4,310,001 A | | 1/1982 | Comben |
| 4,351,345 A | * | 9/1982 | Carney ........................ 607/122 |
| 4,360,025 A | | 11/1982 | Edwards |
| 4,382,445 A | | 5/1983 | Sommers |
| 4,683,895 A | | 8/1987 | Pohndorf |
| 4,777,950 A | | 10/1988 | Kees, Jr. |
| 5,158,097 A | | 10/1992 | Christlieb |
| 5,273,053 A | * | 12/1993 | Pohndorf ...................... 607/132 |
| 5,314,463 A | * | 5/1994 | Camps et al. ................. 607/129 |
| 5,425,751 A | | 6/1995 | Baeten et al. |
| 5,507,289 A | | 4/1996 | Essen-Moller |
| 5,716,392 A | | 2/1998 | Bourgeois et al. |
| 5,755,758 A | | 5/1998 | Woloszko et al. |
| 5,834,051 A | | 11/1998 | Woloszko et al. |
| 5,836,994 A | * | 11/1998 | Bourgeois ..................... 607/40 |
| 5,861,014 A | | 1/1999 | Familoni |
| 5,944,696 A | | 8/1999 | Bayless et al. |
| 6,026,326 A | | 2/2000 | Bardy |
| 6,055,456 A | * | 4/2000 | Gerber ........................ 607/117 |
| 6,083,249 A | | 7/2000 | Familoni |
| 6,139,555 A | | 10/2000 | Hart et al. |
| 6,216,039 B1 | | 4/2001 | Bourgeois |
| 6,327,503 B1 | | 12/2001 | Familoni |

(Continued)

FOREIGN PATENT DOCUMENTS

DE 44 02 058 C1 * 4/1995

(Continued)

OTHER PUBLICATIONS

English Abstract for DE 44 02 058 C1.

*Primary Examiner*—Carl H. Layno
*Assistant Examiner*—Frances P Oropeza
(74) *Attorney, Agent, or Firm*—Shumaker & Sieffert, P.A.

(57) ABSTRACT

An implantable intramuscular lead system, such as for use as a gastric lead, and method of use in which electrodes along the lead are imbedded in tissue. First and second anchors are mounted on an elongate lead. At least the second anchor is movable along the length of the lead relative to the first anchor to capture the tissue between the anchors so that the lead is retained in position. The system facilitates implantation of the lead in tissue, and may be particularly suited for minimally invasive implantation, such as laparoscopically.

59 Claims, 12 Drawing Sheets

U.S. PATENT DOCUMENTS

| | | |
|---|---|---|
| 6,381,499 B1 | 4/2002 | Taylor et al. |
| 6,434,431 B1 | 8/2002 | Camps et al. |
| 6,500,154 B1 | 12/2002 | Hakky et al. |
| 6,643,794 B1 | 11/2003 | Utsugi |
| 7,027,863 B1 * | 4/2006 | Prutchi et al. ............. 607/5 |
| 2001/0025192 A1 | 9/2001 | Gerger et al. |

FOREIGN PATENT DOCUMENTS

| | | |
|---|---|---|
| EP | 0 234 457 B1 | 5/1993 |
| EP | 0 778 047 A2 | 6/1997 |
| EP | 1 048 321 A2 | 11/2000 |
| WO | WO91/18641 | 12/1991 |
| WO | WO98/48889 | 11/1998 |
| WO | WO99/03532 | 1/1999 |
| WO | WO 01/52932 A1 | 7/2001 |
| WO | WO 01/76690 A1 | 10/2001 |

* cited by examiner

IMPLANTABLE MEDICAL DEVICE WITH CAPTIVATION FIXATION

FIELD OF THE INVENTION

This invention relates to systems and methods for anchoring a medical lead or therapy delivery device to tissue.

BACKGROUND OF THE INVENTION

The human body GI tract comprises the esophagus, the stomach, the small intestine, the large intestine, the colon, and the anal sphincter and is generally described as having a tract axis. Like other organs of the body, most notably the heart, these organs naturally undergo regular rhythmic contractions. In particular these contractions take the form of peristaltic contractions and are essential for the movement of food through each of the respective organs. Like the heart, these contractions are the result of regular rhythmic electrical depolarizations of the underlying tissue. With regards to the small intestine and large intestine, normal electrical depolarizations ("slow waves") typically occur at a rate of approximately 15 and 1 beats per minute (bpm) respectively. Similarly, in the stomach, normal slow waves typically occur at a rate approximately 3 bpm. Not all of these depolarizations, however, normally result in a contraction of the organ. Rather contractions occur upon the occurrence of a normal electrical depolarizations followed by a series of high frequency spike activity.

In some individuals, however, either the regular rhythmic peristaltic contractions do not occur or the regular rhythmic electrical depolarizations do not occur or both do not occur. In each of these situations the movement of food may be seriously inhibited or even disabled. Such a condition is often called "gastroparesis" when it occurs in the stomach [30]. Gastroparesis is a chronic gastric motility disorder in which there is delayed gastric emptying of solids or liquids or both.

Symptoms of gastroparesis may range from early satiety and nausea in mild cases to chronic vomiting, dehydration, and nutritional compromise in severe cases. Similar motility disorders occur in the other organs of the GI tract, although by different names.

Diagnosis of gastroparesis is based on demonstration of delayed gastric emptying of a radiolabeled solid meal in the absence of mechanical obstruction. Gastroparesis may occur for a number of reasons. Approximately one third of patients with gastroparesis, however, have no identifiable underlying cause (often called idiopathic gastroparesis). Management of gastroparesis involves four areas: (1) prokinetic drugs, (2) antiemetic drugs, (3) nutritional support, and (4) surgical therapy (in a very small subset of patients.) Gastroparesis is often a chronic, relapsing condition; 80% of patients require maintenance antiemetic and prokinetic therapy and 20% require long-term nutritional supplementation. Other maladies such as tachygastria or bradygastria can also hinder coordinated muscular motor activity of the GI tract, possibly resulting in either stasis or nausea or vomiting or a combination thereof.

The undesired effect of these conditions is a reduced ability or complete failure to efficiently propel intestinal contents down the digestive tract. This results in malassimilation of liquid or food by the absorbing mucosa of the intestinal tract. If this condition is not corrected, malnutrition or even starvation may occur. Moreover nausea or vomiting or both may also occur. Whereas some of these disease states can be corrected by medication or by simple surgery, in most cases treatment with drugs is not adequately effective, and surgery often has intolerable physiologic effects on the body.

For many years, sensing of the peristaltic electrical wave and gastrointestinal stimulation at various sites on or in the GI tract wall of the digestive system or nerves associated therewith have been conducted to diagnose and treat these various conditions. Examples sensing and GI tract stimulation are set forth in commonly assigned U.S. Pat. Nos. 5,507,289, 6,026,326, and 6,216,039, all of which are incorporated herein by reference.

Electrical stimuli are applied from the neurostimulator implantable pulse generator (IPG [50]) through leads and electrodes affixed at sites in the body of the patient or the GI tract wall that permit the electrical stimulus to produce a local contraction of a desired portion of the GI tract. The sites of the GI tract wall comprise the outermost serosa or sub-serosally in the inner, circumferential and longitudinal (and oblique in the case of the stomach) smooth muscle layers referred to as the "muscularis externa". The smooth muscle is preferably comprised of innervated muscle tissue, and it is theorized that the smooth muscle is neurally electrically stimulated through the nerves associated with and innervating the muscle tissue in order to produce the contraction of the smooth muscle.

An implantable method and system for electrical stimulation of smooth muscle with intact local gastric nerves comprising a portion of the GI tract is disclosed in the '607 patent. The electrical stimulation of the smooth muscle effects local contractions at sites of a portion of the GI tract that are artificially propagated distally therethrough in order to facilitate or aid at least a partial emptying of such portion. This stimulation attempts to create a simulated system that reproduces the spatial and temporal organization of normal gastric electrical activity by creating and controlling local circumferential non-propagated contractions. In this simulated gastric pacing system, each local circumferential contraction is invoked by applying an electrical stimulus to the smooth muscle circumferentially about the portion of the GI tract in a plane substantially perpendicular to the longitudinal axis of the portion. The electrical stimulus is applied at a proximal location and at at least one distal location. The distal location is in axially spaced relationship relative to the proximal location. Further, the applied electrical stimulus is selected to be sufficient to stimulate the smooth muscle to produce the local circumferential contractions at the proximal and distal locations.

The Medtronic® Itrel III® Model 7425 IPG and pairs of the unipolar Model 4300 or Model 4301 or Model 4351 "single pass" leads available from MEDTRONIC, INC., Minneapolis, Minn., have been implanted to provide stimulation to sites in the stomach wall to treat chronic nausea and vomiting associated with gastroparesis. The unipolar electrode of these leads comprises a length of exposed lead conductor and is of the type disclosed in commonly assigned U.S. Pat. Nos. 5,425,751, 5,716,392 and 5,861,014, which are incorporated herein by reference. The above-referenced '039 patent and the '014 patent disclose the Model 4300 lead sewn through the serosa laterally into the muscularis externa to dispose the stimulation/sense electrode therein. A large incision is necessary to access the site, and a needle is used to perforate the serosa and muscularis externa laterally without fully penetrating the wall and to draw the stimulation/sense electrode into the muscularis extema. A laparoscopic approach can be taken, but it is difficult to fixate the lead at the implant site The stimulation/sense electrodes conventionally employed in such gastrointestinal stimulation systems are formed of bio-compatible material shaped to either bear against the serosa or penetrate sub-serosally into the muscularis externa and polished to present an impervious outer surface. It is also suggested in the above-referenced '014 patent that the exposed electrode(s) of the single pass lead can alternatively be formed of other biocompatible electrode materials, including porous, platinized structures and could feature various pharmaceutical agents. Suggested pharmaceutical agents include dexamethasone sodium phosphate or beclomethasone phosphate in order to minimize the inflammatory response of the tissue to the implanted lead.

When the stimulation leads are inserted or implanted, they are typically anchored in place by sewing the lead through the serosa laterally into the muscularis externa at both the proximal lead entrance site as well as the distal end of the electrode(s). The anchoring is important for the insertion or implantation procedure because this is intended to prevent the stimulation lead from migrating away from a specifically selected stimulation site. The anchoring process is often used during surgical procedures where there is limited space to anchor and secure the lead to tissue, and time constraints to complete the procedure rapidly. For some procedures, anchor the lead to the stomach wall can be one of the most time consuming and invasive portions of the stimulation lead insertion procedure. Clinicians inserting and anchoring therapy delivery elements typically prefer to perform the procedure rapidly, in a minimally invasive manner, and fix the therapy delivery element in a manner that reduces the opportunity for the therapy delivery element to migrate if practicable. Previous stimulation lead anchoring systems can have one or more of the following limitations along with other limitations such as being difficult to use for minimally invasive procedures, difficult to secure the simulation lead in the desired position and susceptibility to lead migration.

SUMMARY OF THE INVENTION

The invention provides a system and method for anchoring therapy delivery devices and medical leads, such as gastric leads, in tissue. Preferred embodiments of this invention facilitate, among other things, minimally invasive procedures, reliably securing the therapy delivery element or electrodes in position within tissue, and rapid placement to reduce procedure time. The therapy delivery element may be embodied in a tissue stimulation lead adapted to be implanted within the body at a site to conduct electrical stimulation from an implantable or external neurostimulator to the site and to conduct electrical signals the site to the implantable or external neurostimulator.

Exemplary embodiments of the invention pertain to gastrointestinal leads, which are adapted to be implanted within the body at a site of the gastrointestinal tract (GI tract) to conduct electrical stimulation from an implantable or external electrical neurostimulator to the site, and/or to conduct electrical signals of the GI tract from the site to the implantable or external electrical neurostimulator.

In one aspect, an implantable intramuscular lead system generally comprises at least one elongate lead, first and second anchors mounted on the lead. The second anchor is mounted on the lead for movement along the length of the lead relative to the first anchor to capture the tissue between the anchors so that the lead is retained in position. For example, the lead may have at least one electrode (preferably a plurality) along the length of the electrode, and the first and second anchors are mounted along the length of the lead in opposite directions from the electrode so that the electrode is embedded in the tissue.

Preferably, a suitable locking means is provided for locking the second anchor in position along the lead. Examples a crimp band, a re-adjustable locking means (e.g., clamp or staple) for locking the second anchor in position along the lead, or a surgical clip placed on lead adjacent the second anchor to retain the second anchor against the tissue.

Alternatively, one or both of the first and second anchors may be mounted for movement within range. In this case, the range-limited movable anchor may be spring-loaded relative to the lead so that the anchor is biased against the tissue.

In a second aspect of the invention, an implantable therapy delivery system generally comprises: an implantable therapy delivery device (e.g., IPG or drug pump); at least one elongate therapy delivery element (e.g., medical lead) coupled to the implantable therapy delivery device. The therapy delivery element has a length and opposite ends; and first and second anchors mounted on the therapy delivery element. The second anchor is mounted on the therapy delivery element for movement along the length of the therapy delivery element relative to the first anchor to capture the tissue between the anchors so that the therapy delivery element is retained in position for delivery of a therapy.

In a third aspect of the invention, a method of implanting a therapy delivery system generally comprises: (a) providing an elongate therapy delivery element having a length and opposite ends, a first anchor mounted on the therapy delivery element; and a second anchor mounted on the therapy delivery element for movement along the length of the therapy delivery element relative to the first anchor; (b) introducing therapy delivery element through tissue so that the first anchor engages the tissue; (c) advancing the second anchor along the therapy delivery element to capture the tissue between the first and second anchors, thereby retaining the therapy delivery element in position for delivery of a therapy; and (d) coupling and implanting an implantable therapy delivery device to the therapy delivery element.

BRIEF DESCRIPTION OF THE DRAWINGS

These and other advantages and features of the present invention will be more readily understood from the following detailed description of the preferred embodiments thereof, when considered in conjunction with the drawings, in which like reference numerals indicate identical structures throughout the several views, and wherein.

DETAILED DESCRIPTION OF THE PREFERRED EMBODIMENTS

The intramuscular leads and methods of attachment system of the present invention provides the surgeon with more options for therapy delivery element placement within tissue. This invention can be used wherever it is desirable to sense or deliver a therapy to tissue. Examples of applicable areas of application are not limited to but include tissue stimulation including muscular stimulation such as GI tract stimulation and including muscle stimulation used in dynamic gracilo-plasty.

The invention is ideally suited for a gastric stimulation application or other tissue stimulation applications. The invention is particularly useful where it is desirable to impinge a muscle with a stimulation electrode and to captivate the lead within the muscle. The invention is amenable to a quick placement and anchoring through a cannula as commonly used in laparoscopic procedures and other types of minimally invasive surgical techniques.

Figure 1:
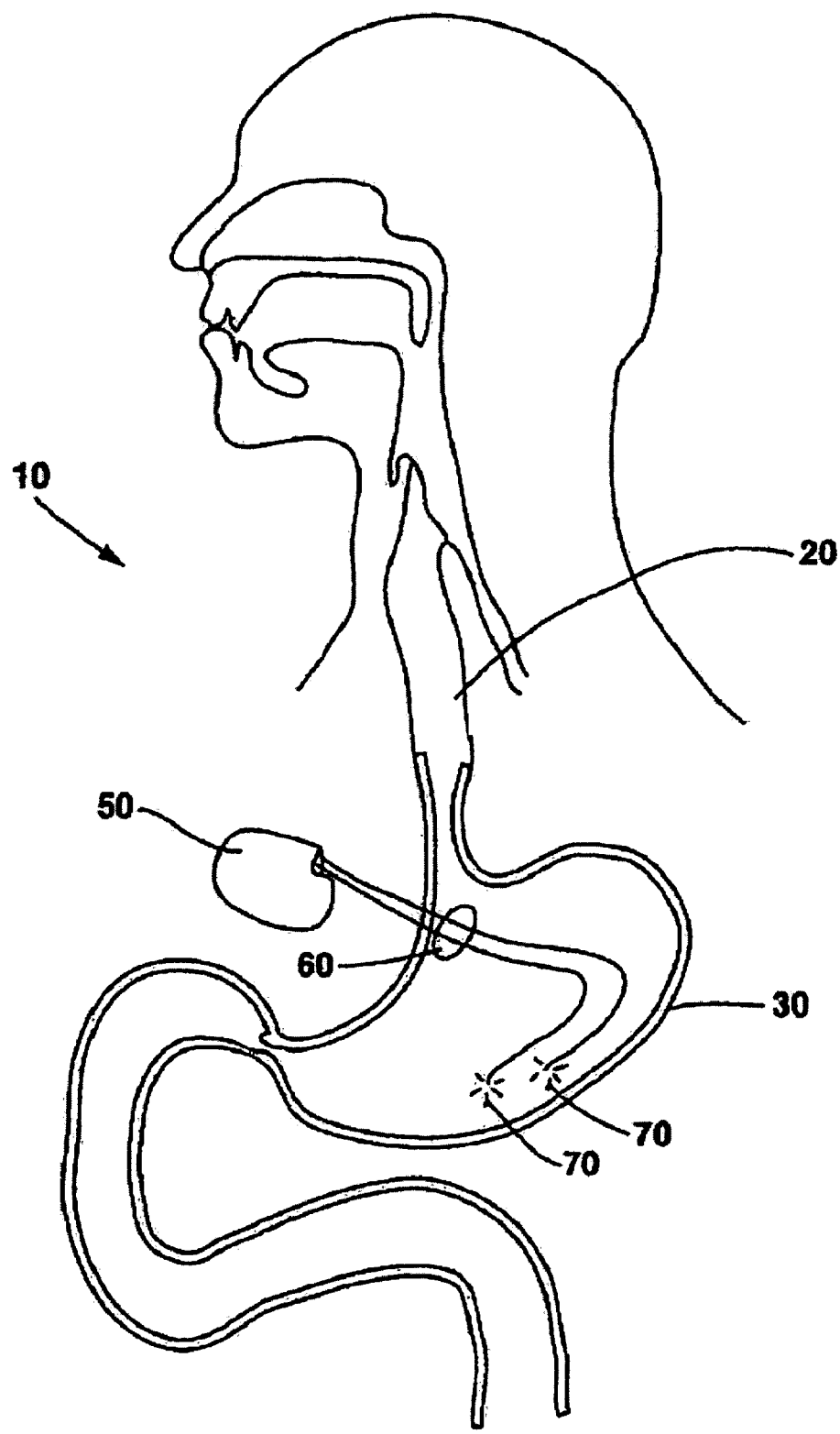
FIG. 1 is an illustration of a patient with a gastric stimulation system implanted.

FIG. 1 is an illustration of a gastric stimulation system [10] implanted in a human body [20], and in particular, the stomach [30] of the human body [20]. The gastric stimulation system [10] includes an IPG [50] including leads [60], which are coupled to the stomach [30] of the patient [20]. Disposed at the end of the leads [60] are electrodes [70].

The IPG [50] can comprise any of the hermetically enclosed IPGs disclosed in the above-listed patents that enclose a battery and an electrical operating system powered by a battery. The IPG [50] operating system can sense the gastro-electrical signals conducted through the electrodes [70], and pulse generator circuitry that generates electrical stimulation pulses that are conducted through the electrodes [70] to the stomach [30] in accordance with a programmed operating mode and programmed operating parameter values. It will be understood that the stimulation/sense electrodes [70] can all function as sensing and stimulation electrodes, and the selection of the stimulation/sense electrodes [70] for sensing and stimulation functions can be programmed into the IPG [50].

Figure 2:
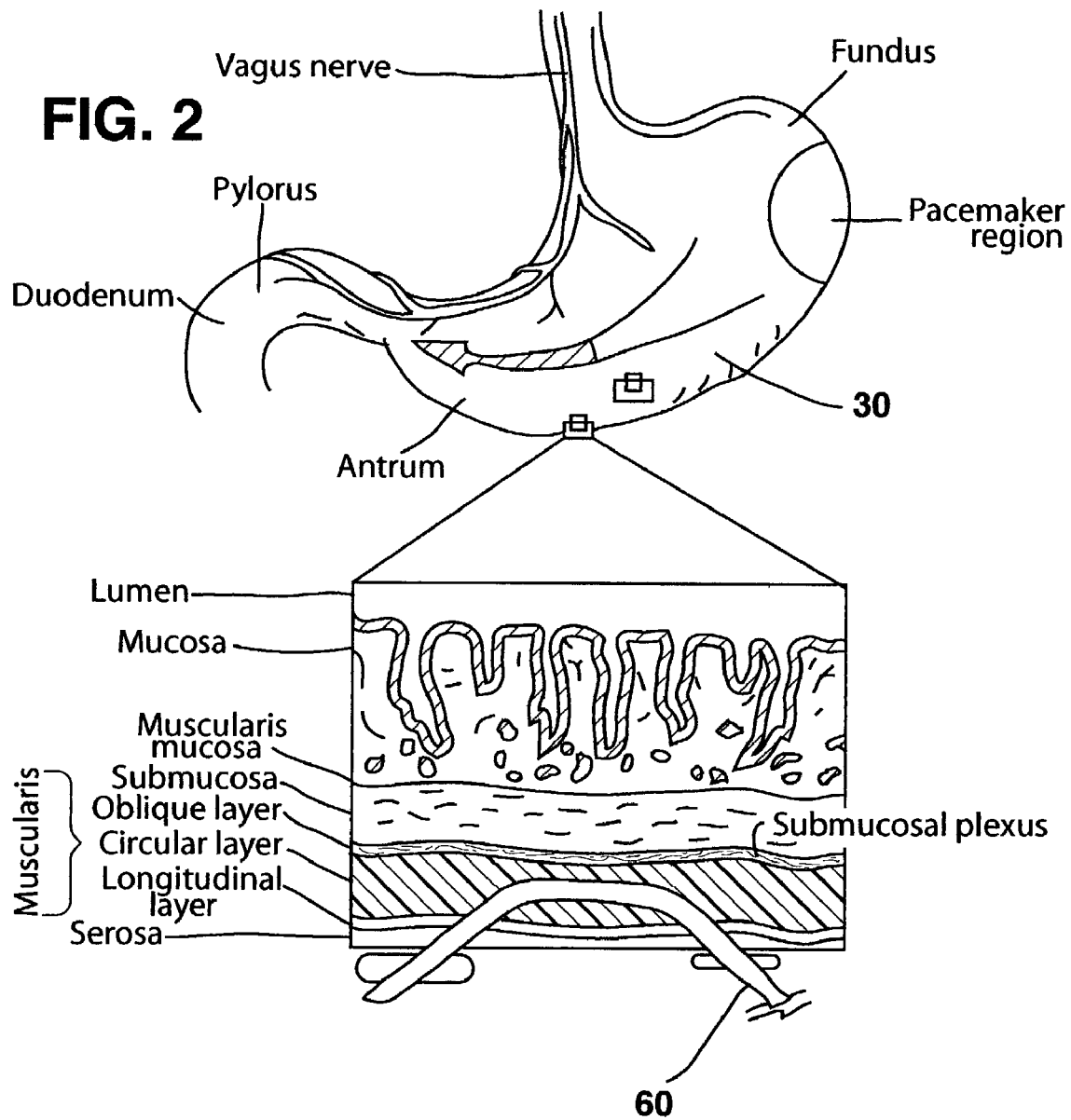
FIG. 2 is an illustration of a gastric lead implanted in gastric tissue.
Figure 3A:
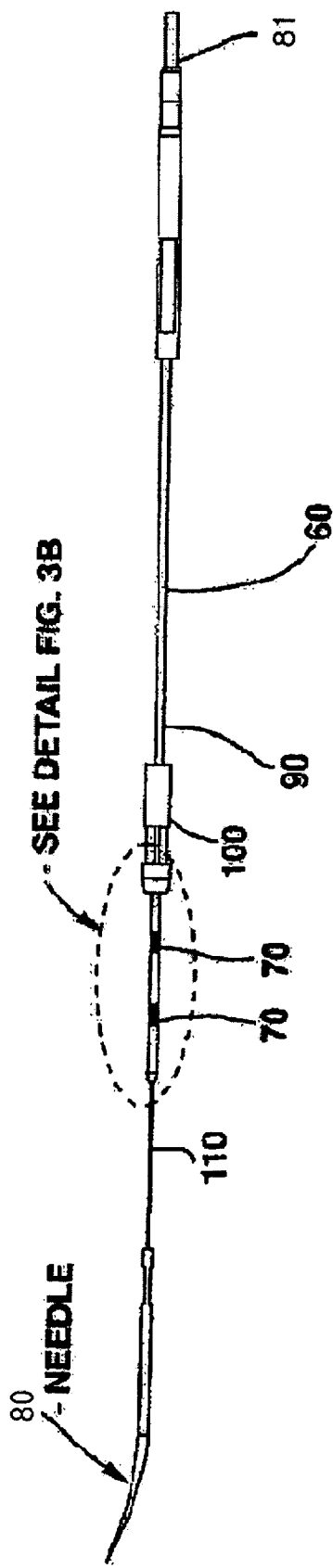
FIG. 3A is a side view of a gastric stimulation lead with an insertion needle.
Figure 3B:
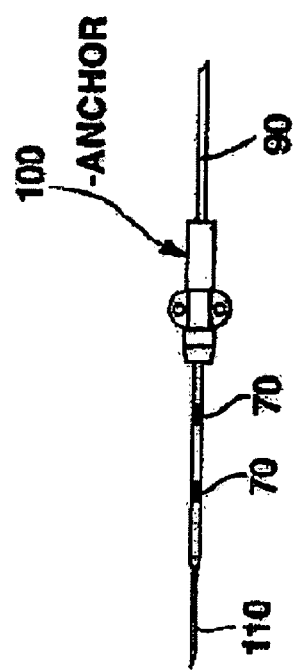
FIG. 3B is an enlarged view of portion 3B of FIG. 3A.

The stomach wall of the stomach [30] comprises essentially seven layers of tissue that are shown in cross-section in FIG. 2. The seven tissue layers include the oblique, circular, and longitudinal muscle layers of the muscularis externa that contract and expand as described above, interposed between the interior stomach mucosa and the external serosa. In the preferred embodiments, the intramuscular lead in FIGS. 3A-B is drawn through the muscle using the integral needle [80] to perforate the serosa and lodge in the electrodes [70] in the muscularis externa, particularly within the thickest circular layer as shown in FIG. 2. The typical depth of penetration of the electrodes [70] is preferably in the range of 1 mm to 15 mm when the site comprises the antrum or in the range of 1 mm to 10 mm when the site comprises corpus or fundus to ensure that the electrodes [70] does not extend substantially through the stomach wall.

FIGS. 3A-B show a stimulation lead [60] embodiment. The implantable stimulation lead [60] configured for laparoscopic implantation has a lead body [90], at least one electrode [70], at least one connector [81], and at least one conductor. The lead body [90] has a distal body end, a proximal body end. The electrode(s) [70] is coupled to the distal body end, and the connector [81] is coupled to the proximal body end. There is a conductor carried in the lead body [90] to electrically connect the electrode [70] to the connector [81]. The conductor is insulated by the lead body [90]. The implantable stimulation lead [60] having one or more isolated electrodes [70], having a diameter of approximately a 0.127 cm (0.050 inch), having an anchor-stop fixed to the lead body [90] proximal to the electrodes [70] to act as a proximal stop [100] and having a suture wire [110] and needle [80] attached to the end of the lead [60] to assist in the introduction of the lead [60] into tissue.

The embodiment shown in FIGS. 3A-B is implanted by utilizing the needle [80] to size the amount of tissue to be captivated between the anchor-stops. The length of the needle [80] is sized to perform the function of as a gauge so the physician can obtain optimal electrode placement. The needle-gauge [80] is used to obtain appropriate insertion depth and to obtain the appropriate amount of tissue to be captivated for stimulation by the electrodes [70]. The diameter of the needle [80] is chosen to allow the lead body [90] to pass through the channel created by the needle [80] without difficulty. The length of the needle [80] is determined by the length of electrode and lead to be imbedded within the tissue along with an additional length to allow manipulation of the needle [80] with the appropriate tool. The shape of the needle [80] is determined by ergonomics and by the need to allow the passage of the lead [60] down a small cannula.

Figure 4:
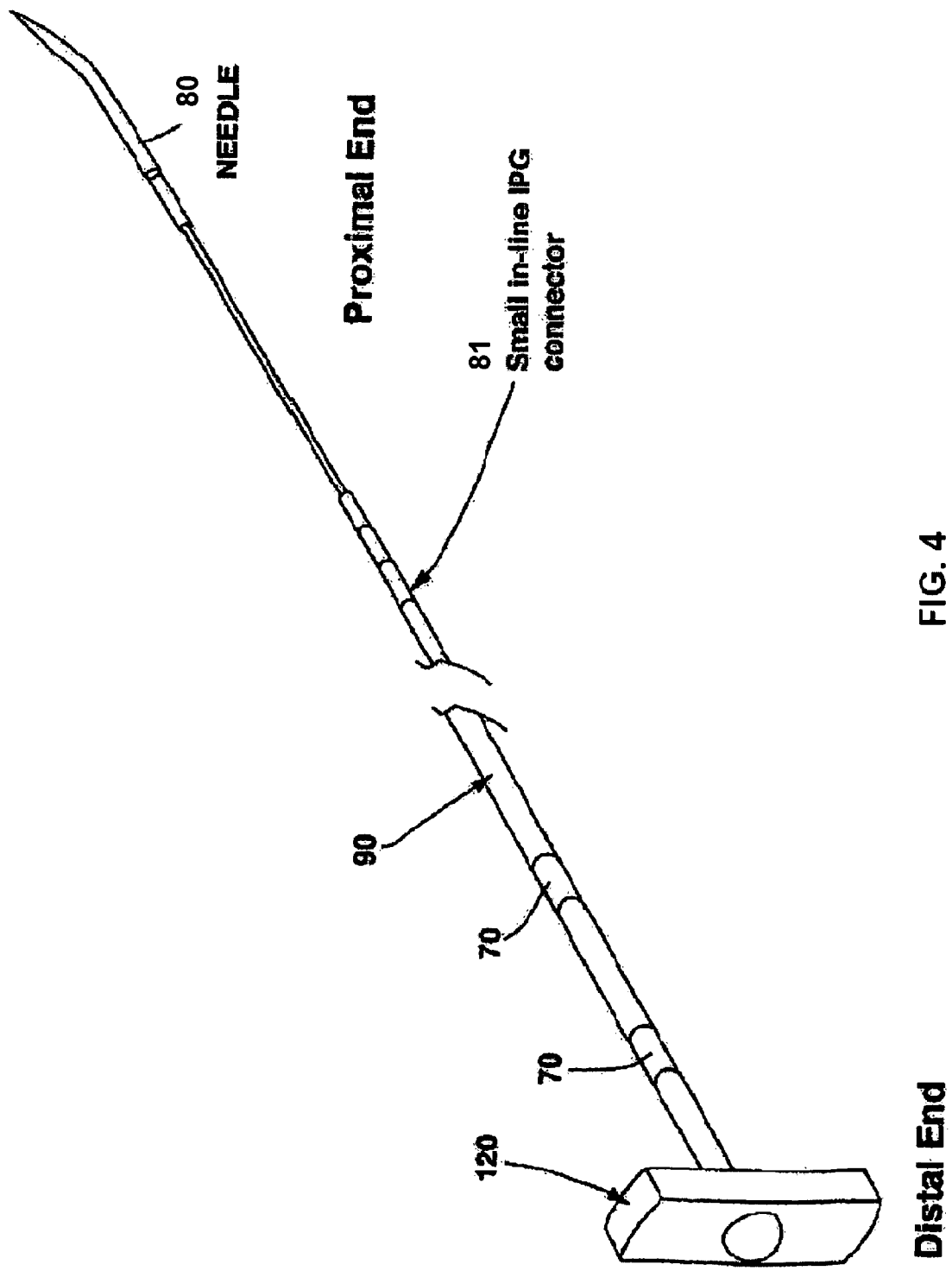
FIG. 4 is a perspective view of a gastric lead with distal anchor and insertion needle.

The embodiment shown in FIG. 4 is an alternative embodiment with the needle [80] attached to the proximal end of the lead body [90] and a fixed anchor [120] attached to the distal end of the lead body [90]. In this manifestation, the lead body [90] is pulled through the muscle until it reaches the pre-attached anchor stop [120] on the most distal end of the lead body [90].

The anchor-stop [100,120] can be permanently attached to the lead body [90]. An alternative embodiment is an anchor that can be sutured or can be permanently fixed to the lead body [90] by other means by the physician. This would be desirable when variability of the tissue stimulation application does not allow a consistent placement of the anchor. When the anchor [100,120] is permanently pre-attached to the lead body [90], the anchor is attached at a distance away from the electrode [70] closest to the exit site to prevent inadvertent stimulation of adjacent bodily fluids or tissue. In a muscle stimulation application, this distance is typically 5 mm but may vary depending on application.

Figure 5:
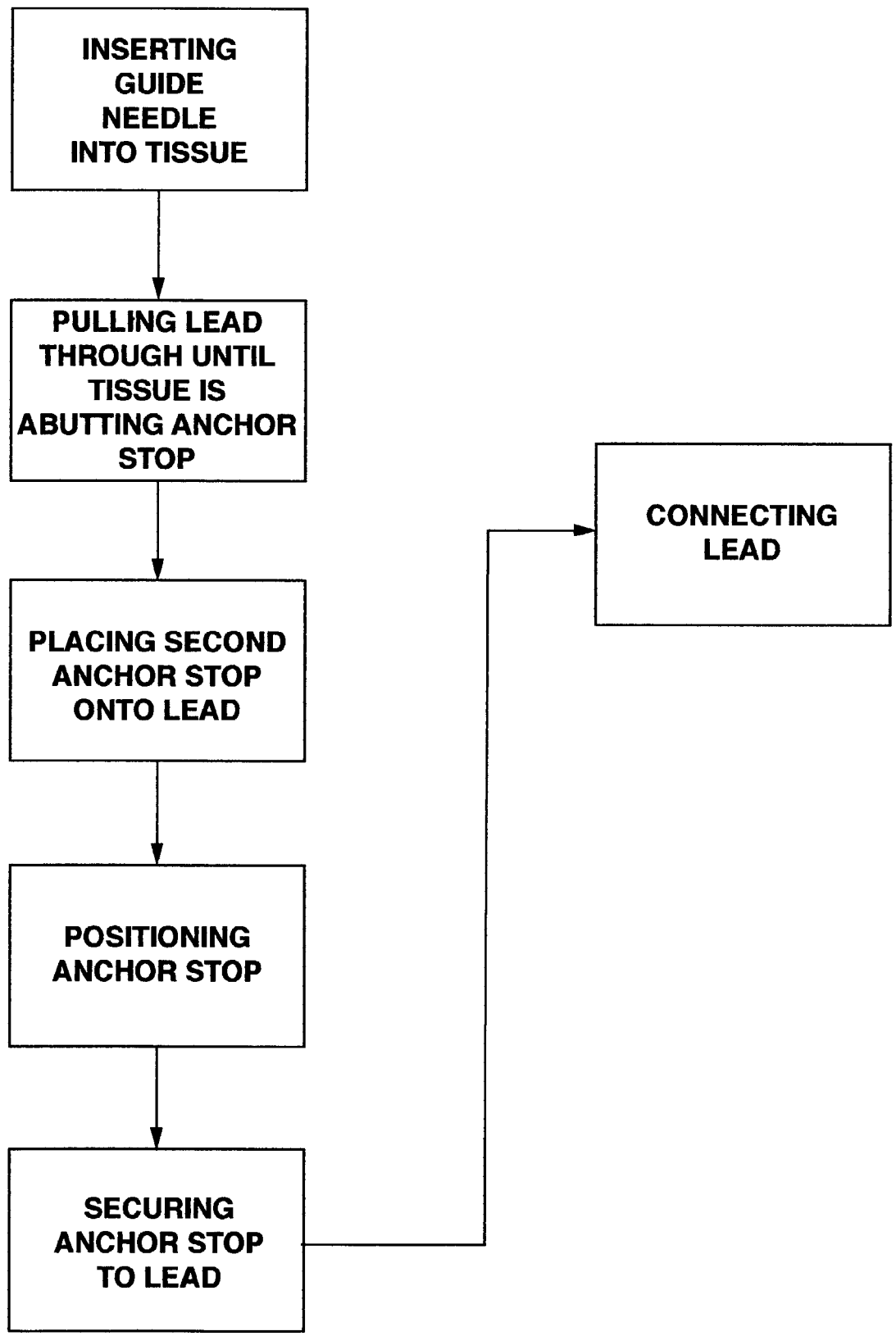
FIG. 5 is a flow chart of a method of implantation of a gastric lead.

The method for implantation of the of the implantable medical device with captivation fixation is shown in FIG. 5. First, the lead [60] is inserted into the target tissue using the guide needle [80] as a gauge to aid in the placement of the electrode(s) [70]. Next, the lead body [90] is pulled through the tissue until the anchor stop [100,120] is abutting tissue adjacent to the targeted stimulation site. Next, a second anchor stop is placed on the lead body [90] and positioned on the lead adjacent on the tissue surface adjacent to the targeted stimulation site and opposite the first anchor stop [100,120]. Next, the second anchor stop is secured to the lead and the lead is connected to the IPG [50].

Figure 6A:
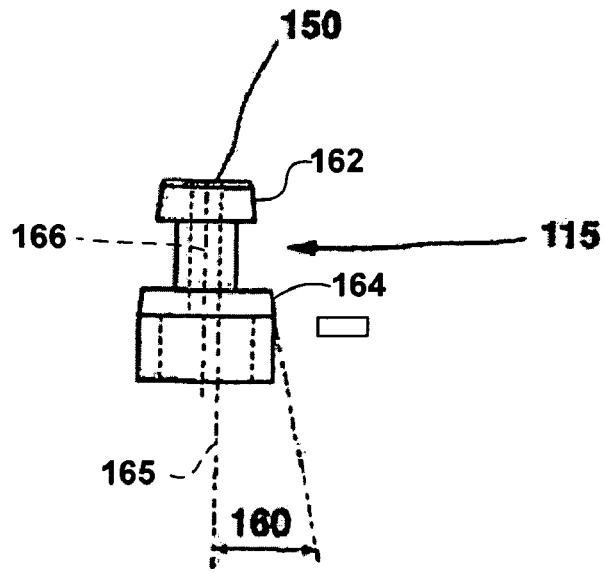
FIGS. 6A-C are side, perspective and cross sectional views, respectively, of an embodiment of an anchor stop.
Figure 6B:
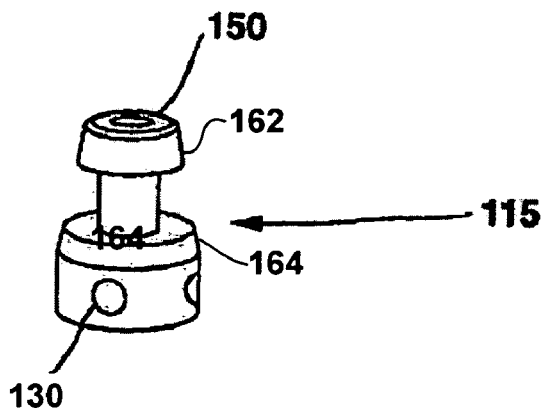
Figure 6C:
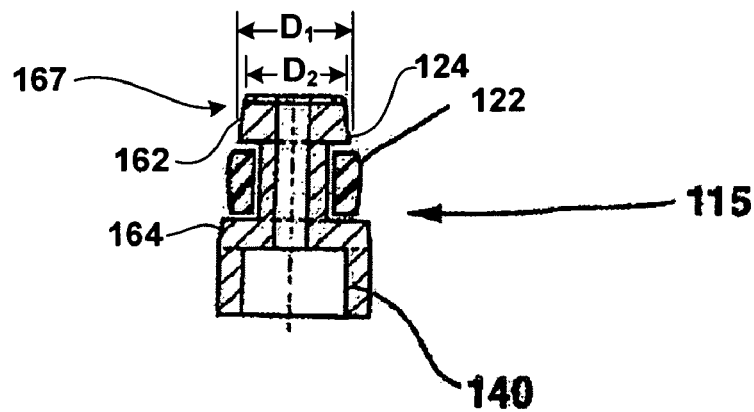

The second anchor (distal anchor in the case of FIGS. 3A-B, proximal anchor in FIG. 4) is inserted on to the lead after the lead [60] has been implanted into the tissue and drawn to the first anchor-stop [100,120]. The second anchor-stop is then advanced to the desired location abutting the tissue and the anchor-stop is coupled to the stimulation lead [60]. Coupling of the anchor-stop to the lead body [90] in proper location is performed through various techniques. In one embodiment shown in FIGS. 6A-C. the anchor-stop [115]

is fixated to the lead body [90] by crimping a band [122] that is an integral part of the anchor-stop assembly [115], causing the anchor-stop [115] to cinch down on the lead body [90]. The band [122] is positioned in a groove [124] defined by the anchor-stop [115]. In this embodiment, indentations or thru holes [130] can be added to allow supplemental anchoring such as suturing. Features to aid in the handling of the lead include a feature [140] to grip the anchor-stop with forceps or other surgical tool. The surface which abuts the tissue [150] is sized large enough to prevent the anchor-stop assembly [115] from being drawn into the tissue; typically 0.125 inches in a gastric application. The anchor-stop [115] may also have surfaces [162, 164] oriented at an angle [160] with respect to a line [165] that is parallel to a center axis [166] of the anchor-stop [115], where the angle [160] is 10 degrees in the gastric application, to allow the anchor-stop [115] to lay flatly against the tissue. As the cross-sectional view of the anchor-stop [115] in FIG. 6C illustrates, the angled surface [162] tapers from a distal diameter $D_1$ to a narrower proximal diameter $D_2$, thereby forming a partial conical-shaped portion [167]. In the embodiment shown in FIG. 6C, distal diameter $D_1$ is also a distal outer perimeter of a portion of the anchor-stop [115], while the proximal diameter $D_2$ is a proximal outer perimeter of the portion of the anchor-stop [115].

Figure 8A:
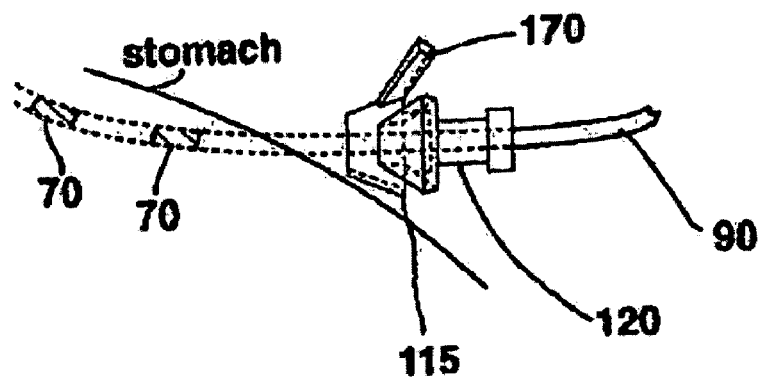
FIGS. 8A-C are side, perspective and back views, respectively, of an embodiment of a side loadable anchor stop with strain-relief fixation wings or tabs.
Figure 8B:
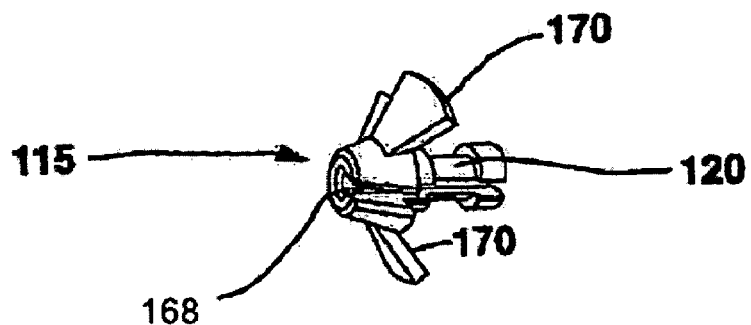
Figure 8C:
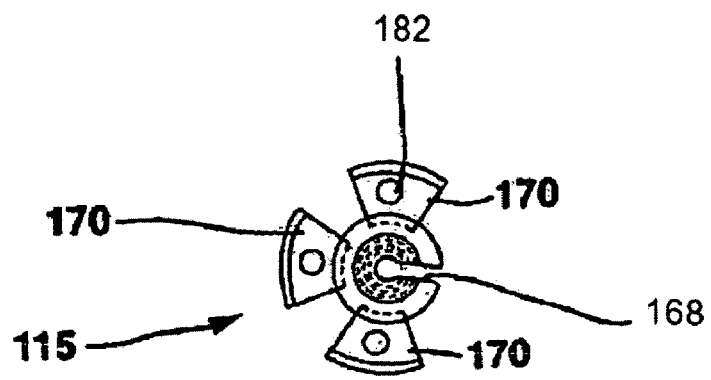

FIGS. 8 A-C show an alternative embodiment with a feature allowing the anchor-stop [115] assembly with a gap [168] running axially to allow the anchor-stop to be applied to the lead body from the side. This feature [168] is desirable in applications such as during a laparoscopic surgery where it may be difficult to insert the anchor onto the lead body [90] axially. This embodiment also contains wings [170] that provide strain relief to prevent the lead from being drawn into the tissue and is fixed to the lead body [90] using a crimp band (e.g., crimp band [122] shown in FIG. 6C). The wings [170] are manufactured from a flexible material such as silicone that will allow the wings [170] to collapse around the anchor-stop body [115] to allow passage through a laprascope. The wings can also contain holes [182] to allow supplemental fixation with sutures.

Figure 7:
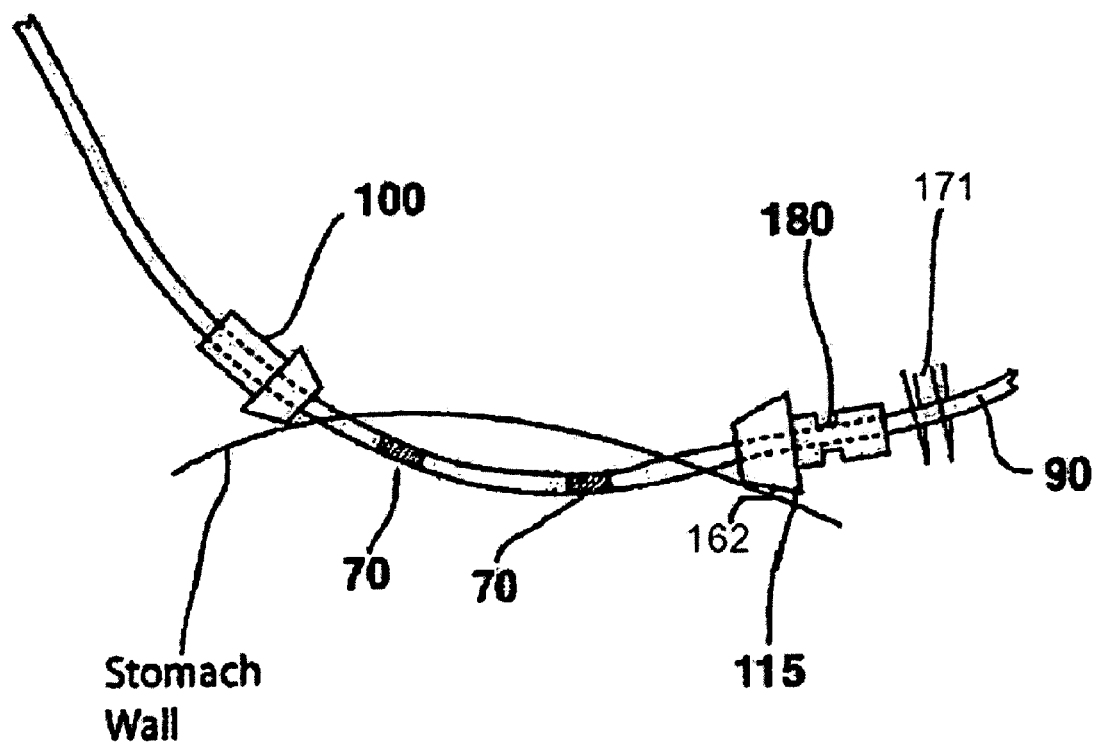
FIG. 7 is an illustration of a gastric lead implanted with the anchor stops of FIGS. 6A-C.
Figure 9A:
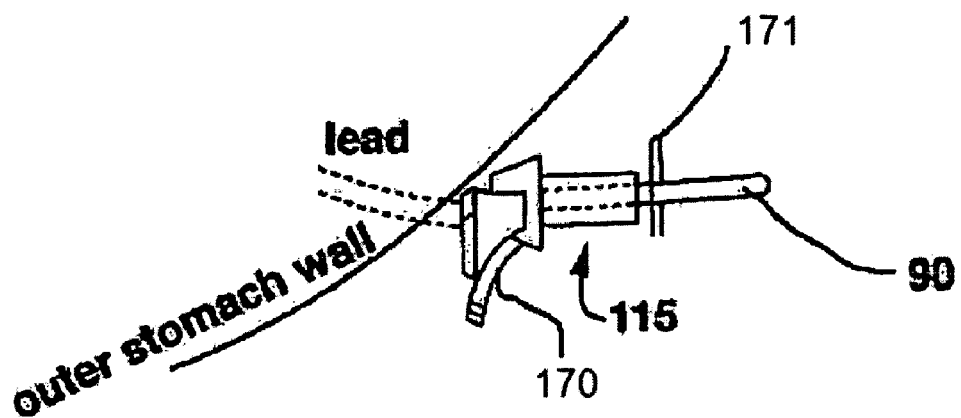
FIGS. 9A-C are side, perspective and back views, respectively, of an embodiment of an anchor stop with strain-relief fixation wings or tabs.
Figure 9B:
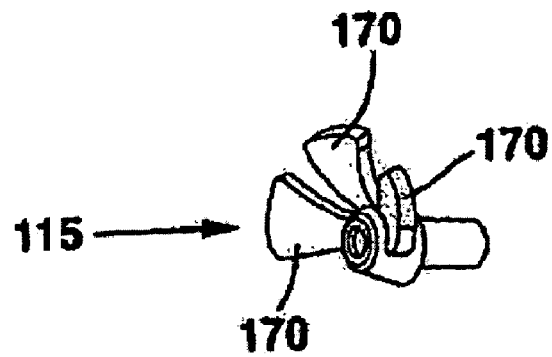
Figure 9C:
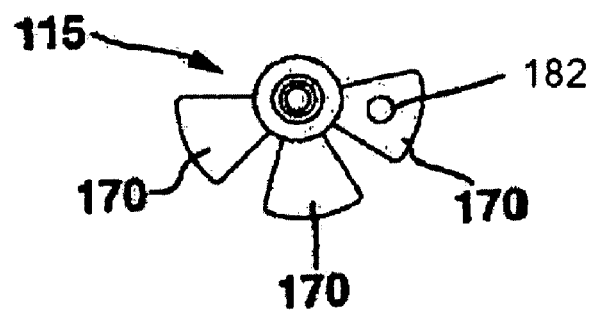

In another embodiment shown in FIG. 7, surgical clips [171] are attached to the lead body [90] behind the anchor [115] thus captivating the electrodes [70] in the tissue between anchor-stop [100] and the anchor-stop [115] and the surgical clips [171]. Alternatively, a suture can be used in a groove [180] in the anchor-stop [115] cinching the anchor-stop [115] onto the lead body [90]. FIGS. 9 A-C show an alternative embodiment utilizing flexible wings [170] that will collapse around the anchor-stop body [115] to allow passage through a laparoscope.

Figure 10A:
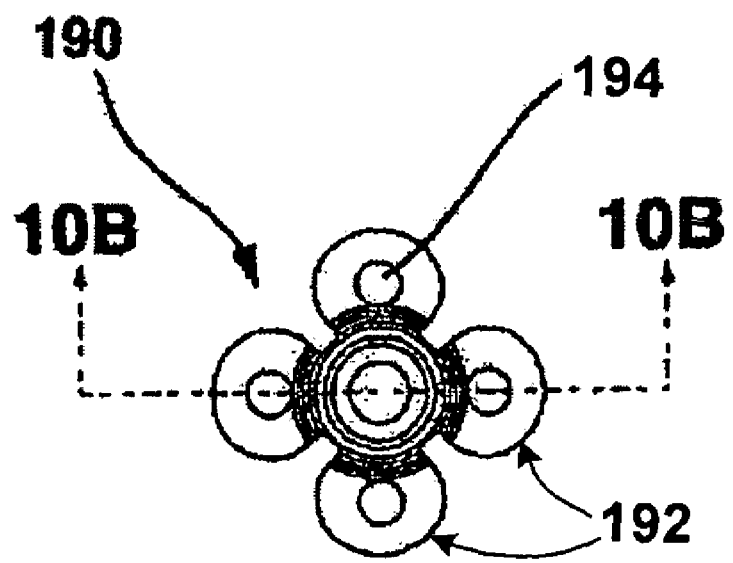
FIGS. 10A-B are back and cross sectional views of an embodiment of a circular anchor with strain-relief fixation wings or tabs.
Figure 10B:
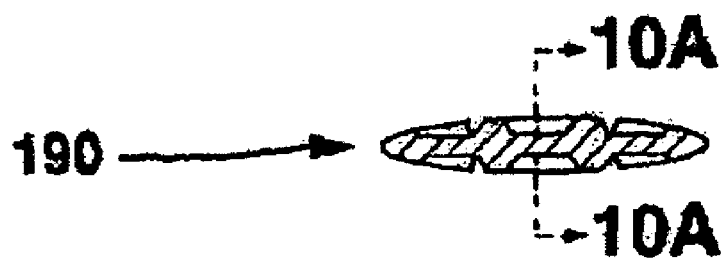

FIGS. 10 A-B show another embodiment of a circular anchor [190] that has wings [192] and can be folded for passage through a laparoscope. The circular folding wings [192] allow for a relatively large surface area for strain relief yet passage through a small diameter laparoscope. The circular folding wings [192] can also contain holes [194] to allow supplemental fixation with sutures.

Figure 11A:
FIGS. 11A-C are side, top and front views, respectively, of another embodiment of an anchor stop.
Figure 11B:
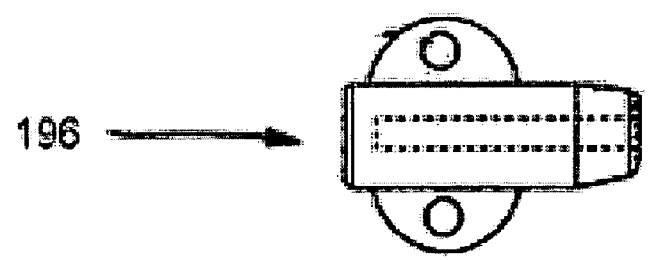
Figure 11C:

FIGS. 11 A-C show an anchor-stop [196] that can be used as a pre-attached anchor stop or could be used in conjunction with surgical clips (e.g., surgical clips [171] shown in FIG. 7) and be used as a distal anchor.

Figure 12A:
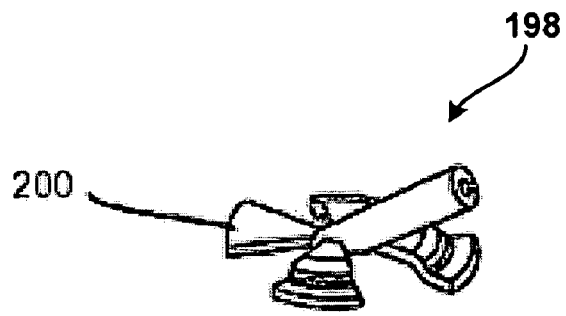
FIGS. 12A-C are perspective, top and side views, respectively of yet another embodiment of the anchor stop.
Figure 12B:
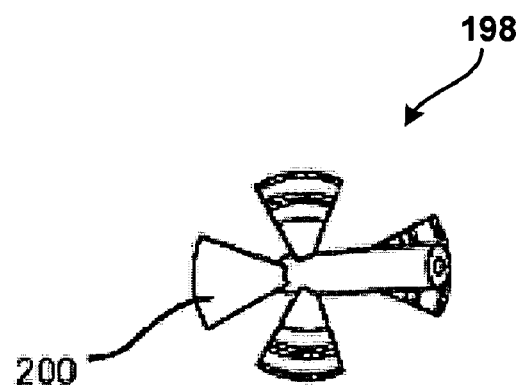
Figure 12C:
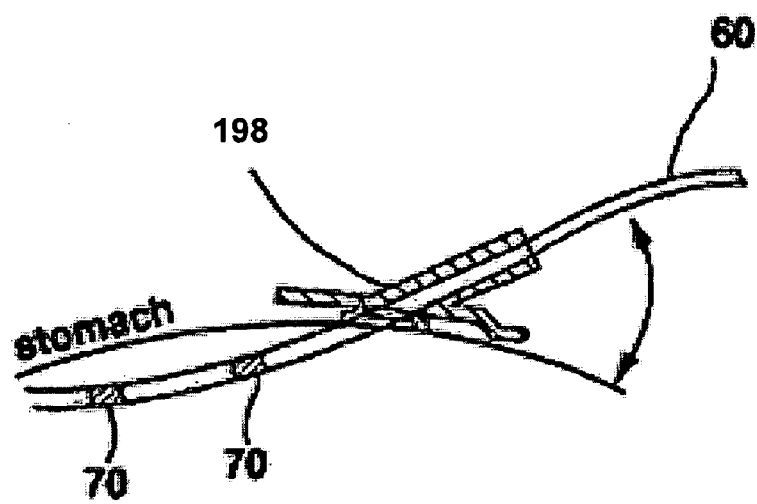

FIGS. 12 A-C show an anchor-stop [198] that can be used as a pre-attached anchor stop [100] or could be used in conjunction with surgical clips and be used as a distal anchor. The flaps [200] along the anchor-stop [198] body are flexible and thus conform to various angles of entry into the muscle. This feature reduces irritation to adjacent tissue and helps the lead conform to a nature entry/exit angle.

An alternative implementation to one fixed anchor and one adjustable anchor would be to have both anchors adjustable along the length of the lead [60] would be advantageous for use penetrating through various thickness of muscle tissue. Both anchors can be moved to maintain the electrodes [70] centered relative to the muscle. Centering electrodes [70] is desirable to help avoid stimulation of adjacent tissue (e.g., outside the target muscle).

The anchor-stops [100,115,190,196] are manufactured from a biocompatible material. In many applications, Silicone is the desired material due to biocompatibility and flexibility. In most applications, flexibility will be desired to avoid irritation of the tissue being stimulated or surrounding tissue.

The anchor-stops [100,115,190,196] contain a feature that abuts the tissue interface to prevent the anchor-stop from being drawn into the tissue. This surface is sized in a manner to distribute the forces acting longitudinally on the stimulation lead to prevent the lead from pulling the anchor into the tissue being stimulated. In a muscle stimulation application such as gastric stimulation or dynamic gracioplasty, this surface is typically a minimum of 0.120 inches. Alternatively, different geometries utilize disks or wings to distribute the forces acting on the anchor-stop/tissue interface.

The longitudinal surface of the anchor-stop is shaped in a manner such that it can lay against the tissue under stimulation without causing trauma to the surface of the tissue under stimulation. The shape of this surface is dependent on the tissue under stimulation as well as the angle of entry/exit of the stimulation lead. In a gastric stimulation application, this shape consists of an angles surface that creates an approximately 10 degree angle. Alternatively, the surface can contain adjustable wings allowing the anchor-stop to take on a range of entry/exit angles.

It should be understood that additional features can be designed into the anchor-stop. An example would be groves within the anchor body to aid in supplemental fixation through the usage of sutures.

In the preferred embodiment, the anchor is designed in a manner that allows insertion into the human body [20] through minimally invasive techniques. State of the art laparoscopic procedures dictate insertion through a 5 to 8 mm cannula. In some embodiments, this requires additional features on the anchor-stop to allow passage to the implant site through a laparoscopic cannula. The anchor-stops shown in FIGS. 3A-B, 4, 6A-C, 7 and 11A-C are smaller than 8 mm diameter. In other embodiments, such as shown in FIGS. 8A-C, 9A-C, 10A-B and 12A-C, the anchor-stop contains flexible features allowing the anchor to have a larger overall diameter while allowing the anchor-stop to be folded-up for insertion through a smaller sized cannula.

Thus, embodiments of the implantable therapy stimulation lead with captivation fixation are disclosed. One skilled in the art will appreciate that the present invention can be practiced with embodiments other than those disclosed. The disclosed embodiments are presented for purposes of illustration and not limitation, and the present invention is limited only by the claims that follow.

The invention claimed is:

1. An implantable intramuscular lead system comprising:
   at least one elongate lead for at least partially implanting in tissue, the lead having a length, and opposite ends;
   a first anchor preattached to the lead; and
   a second anchor mounted on the lead for movement along the length of the lead relative to the first anchor to capture the tissue between the anchors so that the lead is retained in position, a portion of the second anchor comprising a surface configured to abut the tissue, wherein the surface is oriented at an angle with respect to a center axis of the second anchor, wherein the surface tapers from a distal outer perimeter of the portion of the second anchor to a narrower proximal outer perimeter of the portion of the second anchor, wherein the second anchor is mounted on the lead such that the proximal outer perimeter of the portion of the second anchor is located along the lead between the first anchor and the distal outer perimeter of the portion of the second anchor.

2. The lead system of claim 1 in which the lead has at least one electrode along the length of the lead, the first and second anchor being mounted along the length of the lead in opposite directions from the electrode so that the electrode is embedded in the tissue.

3. The lead system of claim 1 in which the lead has a plurality of electrodes along the length of the lead body.

4. The lead system of claim 1 in which the first anchor is movable along the length of the lead.

5. The lead system of claim 1 in which the first anchor is permanently affixed to the lead.

6. The lead system of claim 1 further comprising locking means for locking the second anchor in position along the lead.

7. The lead system of claim 6 in which the looking means comprises a crimp band.

8. The lead system of claim 6 in which the locking means comprises a readjustable locking means for locking the second anchor in position along the lead.

9. The lead system of claim 6 in which the locking means comprises a surgical clip placed on lead adjacent the second anchor to retain the second anchor against the tissue.

10. The lead system of claim 1 in which the first and second anchors are collapsible to allow introduction through a cannula.

11. The lead system of claim 10 in which at least one of the anchors has a plurality of resiliently-foldable wings that are adapted for fixation to the tissue.

12. The lead system of claim 11 in which the wings include suture holes for receiving sutures.

13. The lead system of claim 1 in which at least one of the first and second anchors is mounted for movement within range.

14. The lead system of claim 13 in which at least one of the first and second anchors is spring-loaded relative to the lead so that the anchor is biased against the tissue.

15. The lead system of claim 1 in which the second anchor is separate from the lead but mountable on the lead so that the second anchor can be mounted on the lead after the lead has been inserted in the tissue.

16. The lead system of claim 1 further comprising a line extending from one end of the lead, and a needle attached to the line whereby the needle and line are passed through the tissue and then used to pull the lead through the tissue.

17. The lead system of claim 16 in which the needle has a length corresponding to a desired spacing between the first and second anchors to facilitate placement of the lead in the tissue.

18. The lead system of claim 17 in which the line comprises a polypropylene monofilament line.

19. The lead system of claim 17 in which the line and needle are removable.

20. A combination of a lead system of claim 1 with a delivery system comprising a cannula through which the lead system is introduced, wherein the first and second anchors are adapted to pass through the cannula.

21. The combination of claim 20 in which the first and second anchors are collapsible to allow introduction through the cannula.

22. The combination of claim 21 in which the cannula has a internal diameter of 2-5 mm, the first and second anchors are collapsible to allow passage through the cannula.

23. The combination of claim 20 in which the first and second anchors are sized to allow introduction through the cannula.

24. A combination of the lead system of claim 1 with an implantable pulse generator, the lead being operatively coupled to the implantable pulse generator.

25. The implantable intramuscular lead system of claim 1, wherein the portion of the second anchor defines a partial conical shape wherein the distal outer perimeter of the portion is a distal diameter of the portion and the proximal outer perimeter is a proximal diameter of the portion.

26. The implantable intramuscular lead system of claim 1, wherein the surface of the second anchor that contacts the tissue has a dimension of at least approximately 0.120 inches.

27. The implantable intramuscular lead system of claim 1, wherein the angle of the surface of the second anchor is about 10 degrees.

28. An implantable therapy delivery system, comprising:
an implantable therapy delivery device;
at least one elongate therapy delivery element for at partial implantation in tissue and coupled to the implantable therapy delivery device, the therapy delivery element having a length and opposite ends;
a first anchor preattached to the therapy delivery element; and
a second anchor mounted on the therapy delivery element for along the length of the therapy delivery element relative to the first anchor to capture the tissue between the anchors so that the therapy delivery element is retained in position for delivery of a therapy, a portion of the second anchor comprising a surface configured to abut the tissue, wherein the surface is oriented at an angle with respect to a center axis of the second anchor,
wherein the surface tapers from a distal outer perimeter of the portion of the second anchor to a narrower proximal outer perimeter of the portion.

29. The implantable therapy delivery system of claim 28 in which the implantable therapy delivery device is an implantable pulse generator, and the elongate therapy delivery element is an implantable medical lead.

30. The implantable therapy delivery system of claim 28 in which the implantable therapy delivery device is an implantable drug pump, and the elongate therapy delivery element is a cannula.

31. The implantable therapy delivery system of claim 28 in which the first and second anchors are collapsible to allow introduction through en endoscopic or laparoscopic cannula.

32. The implantabie therapy delivery system of claim 31 in which at least one of the anchors has a plurality of resiliently-foldable wings that are adapted for fixation to the tissue.

33. The implantable therapy delivery system of claim 32 in which the wings include suture holes for receiving sutures.

34. The implantable therapy delivery system of claim 28, wherein the portion of the second archor defines a partial conical shape wherein the distal outer perimeter of the portion is a distal diameter of the portion and the proximal outer perimeter is a proximal diameter of the portion.

35. A method of implanting a therapy delivery system, comprising the following steps:
providing an elongate therapy delivery element having a length and opposite ends, a first anchor preattached to the therapy delivery element; and a second anchor mounted on the therapy delivery element for movement along the length of the therapy delivery element relative to the first anchor;
introducing therapy delivery element through tissue so that the first anchor engages the tissue;
advancing the second anchor along the therapy delivery element to capture the tissue between the first and second anchors, thereby retaining the therapy delivery element in position for delivery of a therapy, a portion of the second anchor comprising a oriented at an angle with respect to a center axis of the second anchor, the surface tapering from a distal outer perimeter of the portion of the second anchor to a narrower proximal outer perimeter of the portion; and
coupling and implanting an implaritable therapy delivery device to the therapy delivery element.

36. The method of claim 35 further comprising the step of locking the second anchor in position along the therapy delivery element after the step of advancing the second anchor along the therapy delivery element to capture the tissue between the first and second anchors.

37. The method of claim 35 further comprising the step of introducing the therapy delivery element through an endoscopic or laparoscopic cannula.

38. The method of claim 37 wherein the step of introducing the therapy delivery element through an endoscopic or laparoscopic cannula includes resiliently collapsing the first and second anchors as they pass through the cannula.

39. The method of claim 35 wherein a line and a needle are provided, the line extending from one end of the therapy delivery element, and the needle being attached to the line,
the step of introducing the therapy delivery element through tissue includes introducing the needle and line through the tissue and pulling the therapy delivery element through the tissue with the line.

40. The method of claim 39 in which the needle has a length corresponding to a desired spacing between the first and second anchors
the step of introducing the therapy delivery element though tissue includes gauging a desired bite of tissue with the needle to facilitate capture of a quantity of tissue to obtain the desired spacing between the first and second anchors.

41. The method of claim 35, wherein the portion of the second anchor defines a partial conical shape wherein the distal outer perimeter of the portion is a distal diameter of the portion and the proximal outer perimeter is a proximal diameter of the portion.

42. A method of implanting an implantable medical lead, comprising the following steps:
providing an elongate medical lead having a length and opposite ends, a first anchor preattached to the lead, and a second anchor mounted on the lead for movement along the length of the lead relative to the first anchor;
introducing the lead through tissue so that the first anchor engages the tissue;
advancing the second anchor along the lead to capture the tissue between the first and second anchors, thereby retaining the lead in position for delivery of a therapy, wherein a portion of the second anchor comprises a surface configured to abut the tissue, the surface being angled with respect to a center axis of the second anchor, and the surface tapering from a distal, outer perimeter of the portion of the second anchor to a narrower proximal outer perimeter of the portion; and
coupling an implantable pulse generator to the lead.

43. The method of claim 42 further comprising the step of locking the second anchor in position along the lead after the step of advancing the second anchor along the lead to capture the tissue between the first and second anchors.

44. The method of claim 43 further comprising the step of introducing the lead through an endoscopic or laparoscopic cannula.

45. The method of claim 44 wherein the step of introducing the lead through an endoscopic or laparoscopic cannula includes resiliently collapsing the first and second anchors as they pass through the cannula.

46. The method of claim 42 wherein a line and a needle are provided, the line extending from one end of the lead, and the needle being attached to the line,
the step of introducing the lead through tissue includes introducing the needle and line through the tissue and pulling the lead through the tissue with the line.

47. The method of claim 46 in which the needle has a length corresponding to a desired spacing between the first and second anchors,
the step of introducing the lead through tissue includes gauging a desired bite of tissue with the needle to facilitate capture of a quantity of tissue to obtain the desired spacing between the first and second anchors.

48. A method of implanting an implantable gastric lead in gastric tissue, comprising the following steps:
providing an elongate medical lead having a length and opposite ends, a first anchor preattached to the lead; and a second anchor mounted on the lead for movement along the length of the lead relative to the first anchor, a portion of the second anchor comprising a surface configured to abut the gastric tissue, wherein the surface is oriented at an angle with respect to a center axis of the second anchor, and wherein the surface tapers from a distal outer perimeter of the portion of the second anchor to a narrower proximal outer perimeter of the portion;
introducing the lead through gastric tissue so that the first anchor engages the gastric tissue; and
advancing the second anchor along the lead to capture the gastric tissue between the first and second anchors, thereby retaining the lead in position for delivery of a therapy or sensing of gastric activity.

49. The method of claim 48 further comprising coupling and implanting an implantable medical device to the lead.

50. The method of claim 48 further comprising coupling and implanting an implantable pulse generator to the lead.

51. The method of claim 48 further comprising the step of locking the second anchor in position along the lead after the step of advancing the second anchor along the lead to capture the gastric tissue between the first and second anchors.

52. The method of claim 48 further comprising the step of introducing the lead through an endoscopic or laparoscopic carinula.

53. The method of claim 52 wherein the step of introducing the lead through an endoscopic or laparoscopic cannula includes resiliently collapsing the first and second anchors as they pass through the cannula.

54. The method of claim 48 wherein a line and a needle are provided, the line extending from one end of the lead, and the needle being attached to the line,
the step of introducing the lead through gastric tissue includes introducing the needle and line through the gastric tissue and pulling the lead through the gastric tissue with the line.

55. The method of claim 54 in which the needle has a length corresponding to a desired spacing between the first and second anchors, the step of introducing the lead through gastric tissue includes gauging a desired bite of gastric tissue with the needle to facilitate capture of a quantity of gastric tissue to obtain the desired spacing between the first and second anchors.

56. The method of claim 48, wherein the portion of the second anchor defines a partial conical shape wherein the distal outer perimeter of the portion is a distal diameter of the portion and the proximal outer perimeter is a proximal diameter of the portion.

57. An implantable intramuscular lead system comprising:

at least one elongate lead having a length extending between opposite ends;

a first anchor mounted on the lead;

a second anchor mounted on the lead for movement along the length of the lead relative to the first anchor to capture the tissue between the anchors so that the lead is retained in position, wherein the second anchor defines a groove; and a crimping band positioned in the groove of the second anchor.

58. The implantable intramuscular lead system of claim 57, wherein the crimping band is integral with the second anchor.

59. A combination of the implantable intramuscular lead system of claim 57 with an implantable pulse generator, the lead being operatively coupled to the implantable pulse generator.

* * * * *

UNITED STATES PATENT AND TRADEMARK OFFICE
CERTIFICATE OF CORRECTION

PATENT NO.        : 7,463,934 B2
APPLICATION NO.   : 10/121484
DATED             : December 9, 2008
INVENTOR(S)       : Carole Tronnes It is certified that error appears in the above-identified patent and that said Letters Patent is hereby corrected as shown below:

Column 10
Line 26, claim 28 "for at partial" should read -- for at least partial --.
Line 60, claim 34 "second archor" should read -- second anchor --.

Column 11
Line 11, claim 35 "comprising a oriented" should read -- comprising a surface oriented --.
Line 40, claim 40 "element though tissue" should read -- element through tissue --.

Column 12
Line 5, claim 44 "claim 43" should read -- claim 38 --.

Signed and Sealed this

Thirtieth Day of June, 2009

JOHN DOLL
*Acting Director of the United States Patent and Trademark Office*